US012594196B2

(12) United States Patent
Sablone

(10) Patent No.: US 12,594,196 B2
(45) Date of Patent: Apr. 7, 2026

(54) METHOD AND APPARATUS FOR PRODUCING PANT-LIKE ABSORBENT SANITARY ARTICLES

(71) Applicant: Fameccanica.Data S.p.A., San Giovanni Teatino (IT)

(72) Inventor: Gabriele Sablone, San Giovanni Teatino (IT)

(73) Assignee: Fameccanica.Data S.p.A., San Giovanni Teatino (IT)

( * ) Notice: Subject to any disclaimer, the term of this patent is extended or adjusted under 35 U.S.C. 154(b) by 544 days.

(21) Appl. No.: 17/979,046

(22) Filed: Nov. 2, 2022

(65) Prior Publication Data

US 2023/0144533 A1 May 11, 2023

(30) Foreign Application Priority Data

Nov. 5, 2021    (EP) ..................................... 21206778

(51) Int. Cl.
| | |
|---|---|
| *A61F 13/15* | (2006.01) |
| *A61F 13/49* | (2006.01) |
| *A61F 13/496* | (2006.01) |
| *A61F 13/76* | (2006.01) |
| *A61F 13/56* | (2006.01) |

(52) U.S. Cl.
CPC .. *A61F 13/15747* (2013.01); *A61F 13/15723* (2013.01); *A61F 13/15756* (2013.01); *A61F 13/15764* (2013.01); *A61F 13/15804* (2013.01); *A61F 13/49011* (2013.01); *A61F 13/496* (2013.01); *A61F 13/76* (2013.01); *A61F 13/565* (2013.01)

(58) Field of Classification Search
CPC .............. A61F 13/49011; A61F 13/496; A61F 13/15804; A61F 13/15747; A61F 13/15756; A61F 13/565
See application file for complete search history.

(56) References Cited

U.S. PATENT DOCUMENTS

| | | | | | |
|---|---|---|---|---|---|
| 8,556,790 | B2* | 10/2013 | Fujita | ................... | B65H 29/241 |
| | | | | | 493/437 |
| 2012/0157282 | A1 | 6/2012 | Schneider | | |
| 2014/0257229 | A1* | 9/2014 | Wang | ................... | A61F 13/496 |
| | | | | | 604/394 |
| 2014/0318695 | A1* | 10/2014 | LaVon | .............. | A61F 13/15804 |
| | | | | | 156/227 |
| 2024/0000623 | A1* | 1/2024 | Umebayashi | ..... | A61F 13/49011 |

FOREIGN PATENT DOCUMENTS

WO        2007070077 A1      6/2007

OTHER PUBLICATIONS

European Search Report dated Apr. 26, 2022. 6 pages.

* cited by examiner

*Primary Examiner* — Scott W Dodds
(74) *Attorney, Agent, or Firm* — RMCK Law Group PLC

(57) ABSTRACT

A method for producing pant-like absorbent sanitary articles, wherein a plurality of absorbent bodies are attached to a single continuous elastic band, which is cut to form a plurality of absorbent sanitary articles in an outspread configuration, which are then folded in a closed pant-like configuration.

8 Claims, 12 Drawing Sheets

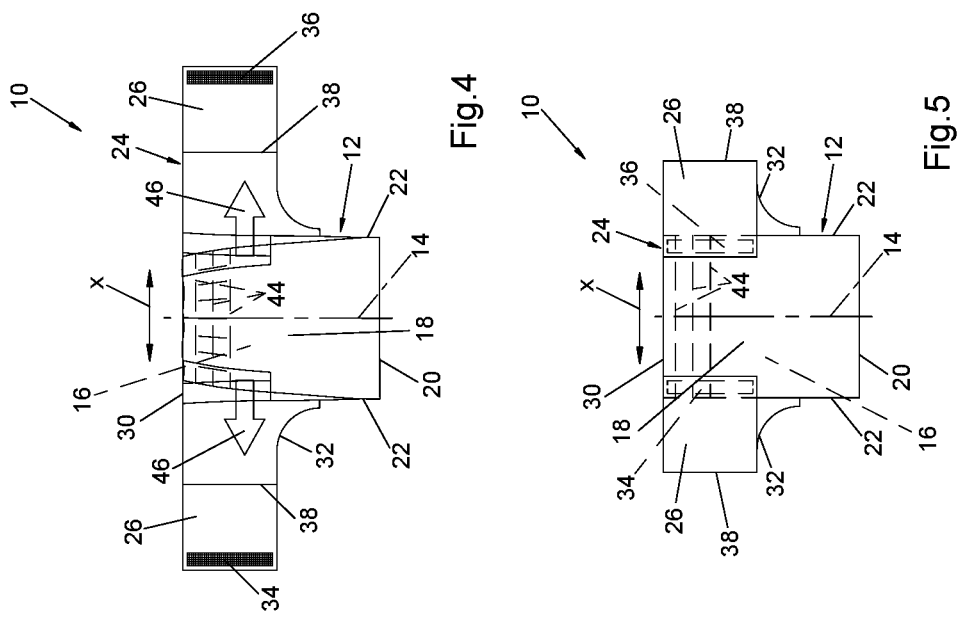
Fig.4
Fig.5
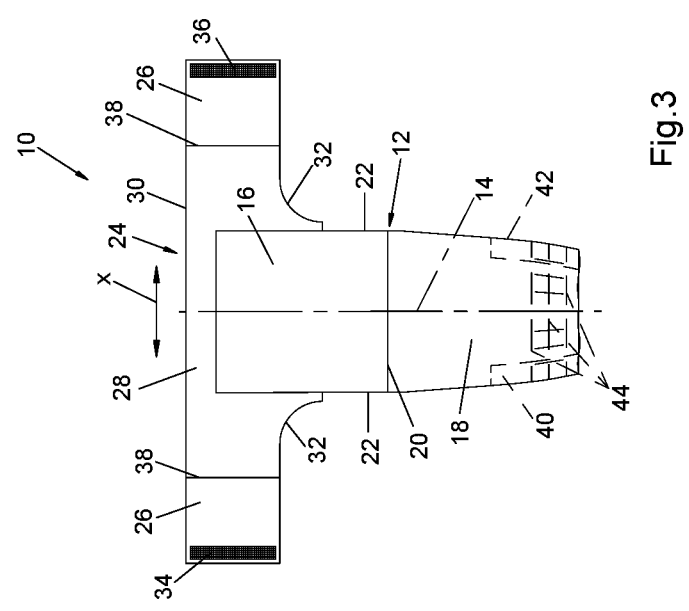
Fig.3

METHOD AND APPARATUS FOR PRODUCING PANT-LIKE ABSORBENT SANITARY ARTICLES

CROSS-REFERENCE TO RELATED APPLICATION

This application claims priority to European Patent Application No. 21206778.9 filed Nov. 5, 2021. The disclosure of the above application is incorporated herein by reference in its entirety.

TECHNICAL FIELD

The present invention relates to a method and apparatus for producing absorbent sanitary articles.

The invention has been developed in particular for producing absorbent sanitary articles wearable as pants, for example the so-called training pants.

More specifically, the invention is directed to the production of refastenable absorbent sanitary articles, which can be opened and reclosed while worn by the user.

The present invention relates in particular to a method and an apparatus for producing absorbent sanitary articles according to the production technique called "Cross Direction".

BACKGROUND ART

A consolidated technique for producing absorbent sanitary articles wearable as pants (both permanently closed and reclosable) consists of forming a continuous composite web movable in a machine direction and formed by a continuous chain of product blanks which are positioned with the longitudinal axis of each individual article transversal with respect to the machine direction. This production technique is normally called "Cross Direction" and differs from the more traditional production technique called "Machine Direction" which involves producing the absorbent sanitary articles while they advance with their longitudinal axes parallel to the machine direction.

Examples of methods for producing absorbent sanitary articles according to the Cross Direction technique are described in documents EP-A-1013251, IT1379452, IT1410464 and IT1410465 by the same Applicant.

The continuous composite web forming the chain of product blanks may comprise two elastic bands which are parallel to the machine direction and spaced apart from each other in a direction orthogonal to the machine direction, and a plurality of absorbent cores which extend between the two elastic bands orthogonally to the machine direction. The continuous composite web advancing in the machine direction is folded along longitudinal axis parallel to the machine direction, so that said elastic bands overlap onto each other.

For producing absorbent sanitary articles which are openable and reclosable, refastenable closure elements are applied on the continuous composite web in spaced apart positions. The refastenable closure elements connect opposite portions of the continuous composite web after the longitudinal folding of the continuous composite web, as disclosed for instance in EP-A-3498246 of the same Applicant.

In traditional methods for producing absorbent sanitary articles according to the Cross Direction technique, the closure elements of the absorbent sanitary articles are usually located on the sides of the waistbands of the absorbent sanitary articles. The presence of refastenable closure elements on the sides of the absorbent sanitary articles may be undesired. Users may prefer absorbent sanitary articles in which the closure zones of the waistbands are positioned on the front waistband rather than along the sides to improve comfort and appearance.

U.S. Pat. No. 6,447,628 describes a method for producing reclosable absorbent sanitary articles in which the closure elements of the waistbands are located on the front parts of the articles. This arrangement is obtained by making a continuous chain of blanks of absorbent sanitary articles which have front waist regions with a shorter length than the rear waist regions. To produce absorbent sanitary articles of this type with a Cross Direction production technique, it is necessary to remove longitudinal stretches of one of the two waistbands of the continuous composite web. In the method described in this document, the removal of portions of one of the waistbands is performed before the longitudinal folding of the continuous composite web. This solution is difficult to implement in practice because after the removal of the portions of one of the longitudinal bands of the continuous composite web it becomes very difficult to perform the longitudinal folding of the continuous composite web with the necessary precision.

Object and Summary

This object of the present invention is to provide a method and apparatus for producing absorbent sanitary articles which overcome the problems of the prior art. More specifically, the object of the present invention is to provide a method and an apparatus for producing refastenable pant-like absorbent sanitary articles which reduces the waste of raw material, and which improves the stability and the quality of the manufacturing process.

According to the present invention, these objects are achieved by a method and by an apparatus as may be set forth in one or more of the following claims.

The claims are an integral part t of the teaching provided herein in relation to the invention.

BRIEF DESCRIPTION OF DRAWINGS

The present invention will now be described in detail with reference to the accompanying drawings, given purely by way of non-limiting example, in which:

FIGS. 3, 4, 5 are schematic views of another embodiment of an absorbent sanitary article in outspread, partially closed, and closed configurations, respectively.

It should be appreciated that the attached drawings are schematic and not to scale with respect to real products and that various figures may not be represented in the same scale. Also, in various figures some elements may not be shown to better show other elements.

DETAILED DESCRIPTION

Figure 2:
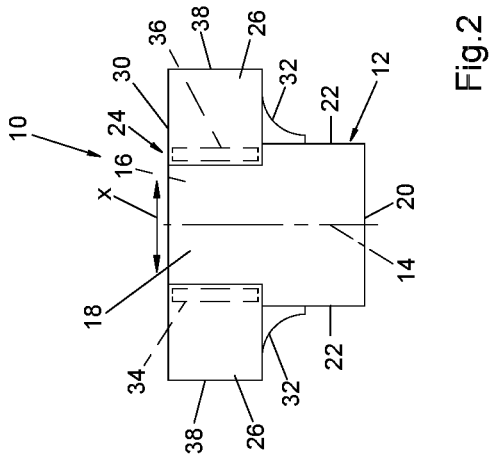
FIGS. 1 and 2 are schematic views of an embodiment of an absorbent sanitary article in outspread and closed configurations, respectively.
Figure 1:
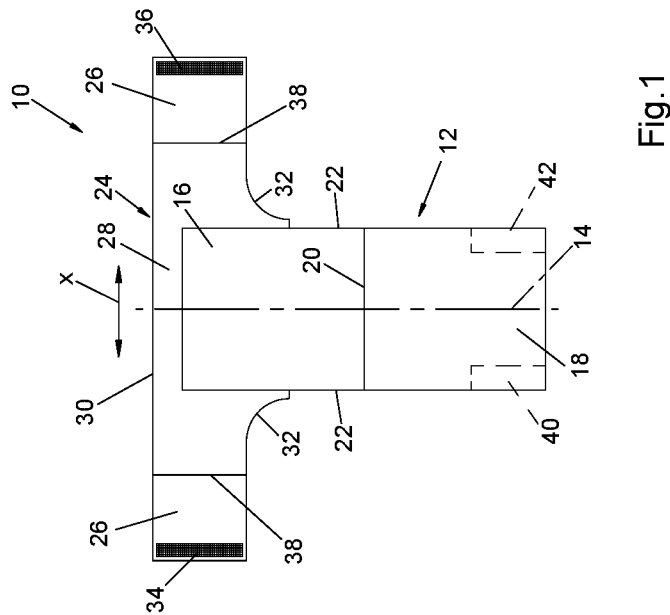

FIGS. 1 and 2 show a first embodiment of a refastenable pant-like absorbent sanitary article 10, respectively in an outspread configuration and in a closed configuration. In the closed configuration the refastenable absorbent sanitary article 10 has a pant-like shape typical of the so-called training pants.

The refastenable pant-like absorbent sanitary article 10 comprises an absorbent body 12 elongated along a main direction 14 and having first and second end portions 16, 18 opposite to each other with respect to a first folding line 20 orthogonal to the main direction 14 of the absorbent body 12. In the closed configuration shown in FIG. 2 the absorbent body 12 is folded about the first folding line 20 and the first and second end portions 16, 18 are overlapped to each other.

The absorbent body 12 has two side edges 22 extending along the main direction 14. The side edges 22 may be straight and parallel to the main direction 14 as shown in the drawings. Alternatively, the side edges 22 may be curved to conform to the legs of the user when the refastenable pant-like absorbent sanitary article 10 is worn.

The absorbent body 12 may comprise an absorbent core enclosed between a topsheet of permeable material and a backsheet of impermeable material. The absorbent body 12 may also comprise elastic leg cuffs attached to the topsheet and extending parallel to the main direction 14, as customary in the field. The absorbent body 12 may also comprise leg elastics extending along the side edges 22.

The refastenable pant-like absorbent sanitary article 10 comprises a single elastic waistband 24 attached to the first end portion 16 of the absorbent body 12. The elastic waistband 24 is elongated along a direction X transverse to the main direction 14 of the absorbent body 12. The elastic waistband 24 is elastically stretchable along the direction X and may comprise a plurality of elastic wires enclosed between two non-woven layers.

The elastic waistband 24 has two elastic lateral bands 26 projecting laterally from opposite side edges 22 of the absorbent body 12, and a central portion 28 attached to the first end portion 16 of the absorbent body 12. The central portion 28 of the elastic waistband 24 may be attached, e.g. by glue, to the backsheet of the absorbent body 12. In the central portion 28 the elastic elements of the elastic waistband 24 may be deactivated, e.g. by cuts that interrupt the elastic wires.

The elastic waistband 24 has an outer edge 30 and an inner edge 32. The outer edge 30 may be straight and transverse to the main direction 14 of the absorbent body 12 and may project beyond a transverse edge of the absorbent body 12. The inner edge 32 may be shaped to conform to the legs of the user when the refastenable pant-like absorbent sanitary article 10 is worn.

The lateral bands 26 of the elastic waistband 24 have respective first and second refastenable closure elements 34, 36 attached to respective distal portions. The refastenable closure elements 34, 36 may be micro-hook closure elements or refastenable adhesive elements. In the distal portions of the elastic waistband 24 where the refastenable closure elements 34, 36 are attached the elastic elements of the elastic waistband 24 may be deactivated, e.g. by cuts that interrupt the elastic wires.

The first and second refastenable closure elements 34, 36 may have areas with differential closure strength, which may be obtained through:

shape of the first and second refastenable closure elements 34, 36 (e.g. trapezoidal instead of rectangular);

micro-hook density variable on the surface of the first and second refastenable closure elements 34, 36;

any other which provides differential means closure strength.

In the closed configuration of FIG. 2, the lateral bands 26 of the elastic waistband 24 are folded about respective second folding lines 38. The second folding lines 38 may be parallel to the main direction 14 and orthogonal to the first folding line 20.

In the closed configuration of FIG. 2, the first and second refastenable closure elements 34, 36 releasably engage respective engagement areas 40, 42 on the backsheet of the absorbent body 12. The engagement areas 40, 42 may be suitable for establishing a releasable surface connection with micro-hook closure elements and may be formed by portions of a frontal tape of loop material or by portions of a non-woven layer applied on the backsheet of the absorbent body 12.

When the absorbent sanitary article 10 is worn, the refastenable closure elements 34, 36 are positioned on the front waist portion of the user and the elastic lateral bands 26 are smooth on the sides of the user, which is advantageous when the absorbent sanitary article 10 is worn beneath the garments.

FIGS. 3-5 show a second embodiment of a refastenable pant-like absorbent sanitary article 10. The elements corresponding to those previously described are indicated by the same numeral references.

In the embodiment of FIGS. 3-5, the second end portion 18 of the absorbent body 12 is provided with transverse elastic elements 44 so that the second end portion 18 is elastically stretchable in the direction X transverse to the main direction 14. Accordingly, in the outspread configuration shown in FIG. 3 the second end portion 18 of the absorbent body 12 is tapered towards the distal end of the absorbent body 12, opposite to the elastic waistband 24.

In this embodiment, during the folding of the absorbent body 12 about the first folding line 20, the second end portion 18 of the absorbent body 12 is stretched in the direction X as shown by the arrows 46 in FIG. 4, so that the engagement areas 40, 42 are brought in a position in which they are parallel to the respective first and second refastenable closure elements 34, 36. Therefore, when the elastic lateral bands 26 of the elastic waistband 24 are folded about the respective second folding lines 38, the first and second refastenable closure elements 34, 36 overlap and engage the respective engagement areas 40, 42.

FIG. 5 shows the closed configuration of the refastenable pant-like absorbent sanitary article 10, after folding the absorbent body 12 about the first folding line 20, transversally stretching the second end portion 18 and folding the lateral bands 26 about the second folding lines 38.

Figure 7:
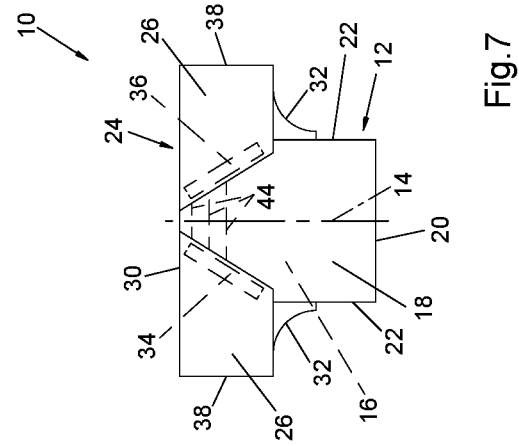
FIGS. 6 and 7 are schematic views of yet another embodiment of an absorbent sanitary article in outspread and closed configurations, respectively.
Figure 6:
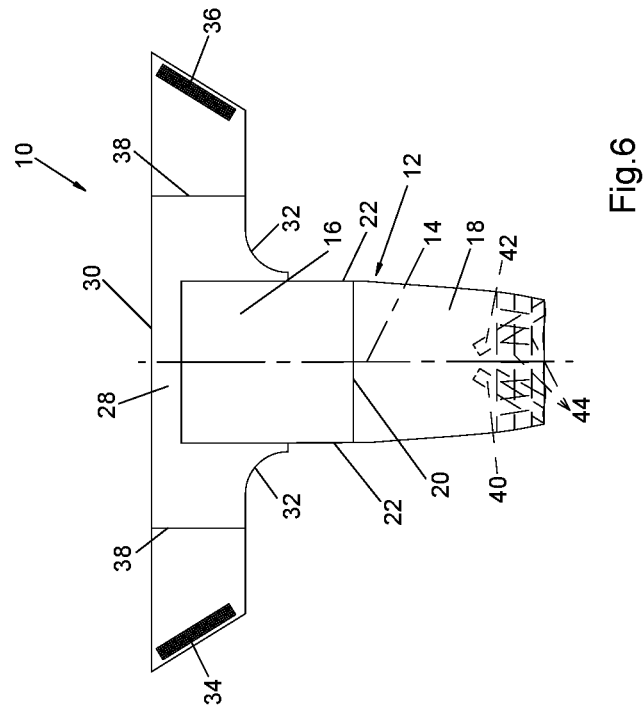

FIGS. 6 and 7 show a third embodiment of a refastenable pant-like absorbent sanitary article 10. The elements corresponding to those previously described are indicated by the same numeral references.

In the embodiment of FIGS. 6 and 7 the first and second refastenable closure elements 34, 36 are inclined with respect to the folding lines 38. The distal edged of the lateral bands 26 may be cut along inclined lines parallel to the respective first and second refastenable closure elements 34, 36.

In the closed configuration of the refastenable pant-like absorbent sanitary article 10 shown in FIG. 7 the first and second refastenable closure elements 34, 36 extend along respective directions which are inclined to the main direction 14. The inclined arrangement of the closure formations is designed to improve the comfort of the refastenable pant-like absorbent sanitary article 10 when worn.

Also in this embodiment, the second end portion 18 of the absorbent body 12 may be provided with transverse elastic elements 44 so that in the outspread configuration shown in FIG. 6 the second end portion 18 of the absorbent body 12 is tapered towards the distal end of the absorbent body 12. Also in this embodiment, during the folding of the absorbent body 12 about the first folding line 20, the second end portion 18 of the absorbent body 12 may be stretched in the direction X.

Figure 8:
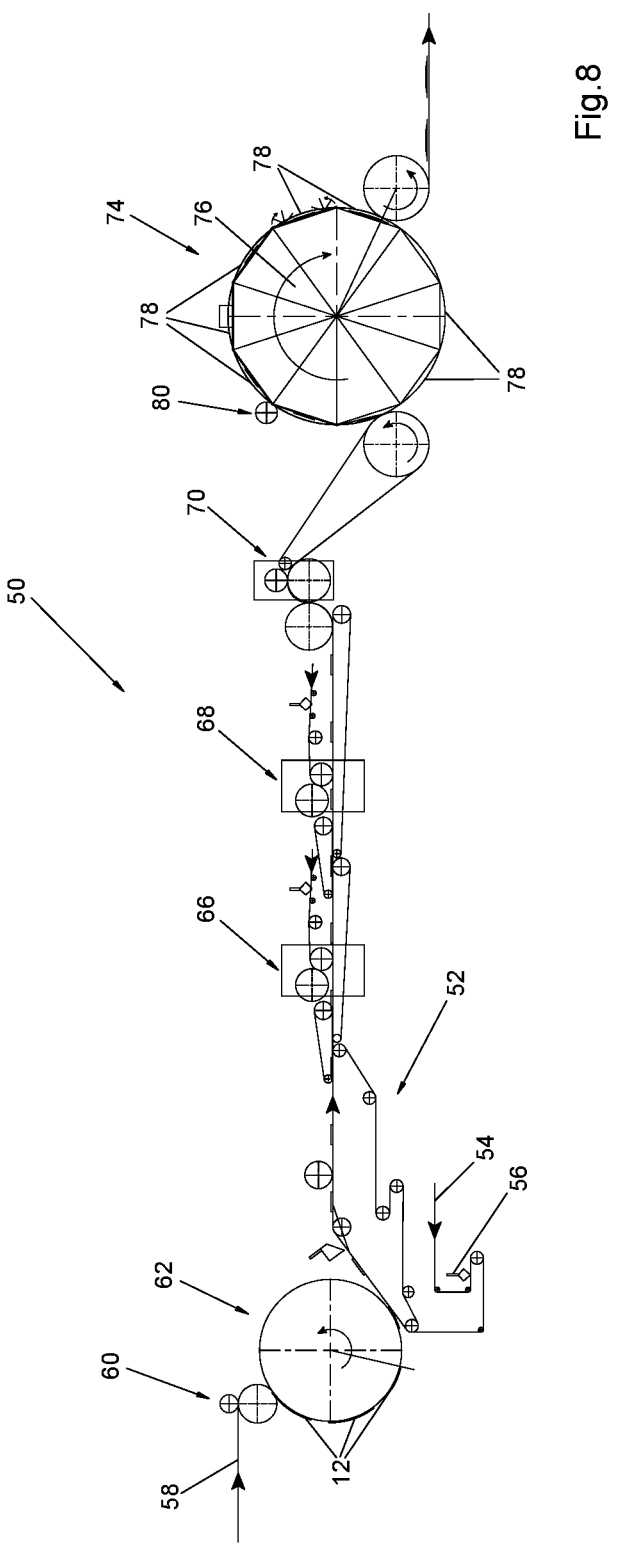
FIG. 8 is a schematic side view of an apparatus for producing absorbent sanitary articles.

With reference to FIG. 8, numeral reference 50 indicates an apparatus for producing refastenable pant-like absorbent sanitary articles 10 as previously disclosed.

The apparatus 50 comprises a conveyor 52 configured for advancing in a longitudinal direction a continuous elastic band 54. A glue dispenser 56 may be provided for applying discrete glue layers on a surface of the continuous elastic band 54.

A continuous composite absorbent web 58 is fed to the apparatus 50 in a longitudinal direction. The continuous composite absorbent web 58 comprises a continuous absorbent core enclosed between a continuous backsheet and a continuous topsheet. The continuous composite absorbent web 58 may comprise continuous longitudinal leg cuffs, continuous longitudinal leg elastics and transverse elastic elements 44 spaced apart from each other in the longitudinal direction.

The apparatus 50 comprises a transverse cutting unit 60 configured for transversely cutting the continuous composite absorbent web 58 to form individual absorbent bodies 12. At the exit of the transverse cutting unit 60 the individual absorbent bodies 12 are oriented with the respective main directions 14 parallel to the moving direction.

The apparatus 50 comprises a turn-and-repitch unit 62, comprising a plurality of gripping elements which are configured for retaining respective absorbent bodies 12, e.g. by suction. The gripping elements of the turn-and-repitch unit 62 take respective absorbent bodies 12 at the transverse cutting unit 60 and turn the individual absorbent bodies 12 by 90° such that the individual absorbent bodies 12 are oriented with the respective main directions 14 transverse to the moving direction. The gripping elements of the turn-and-repitch unit 62 are rotatable independently of each other around a common axis of rotation and are configured to space from each other the individual absorbent bodies 12 at an application pitch.

The individual absorbent bodies 12 are transferred from the gripping elements of the turn-and-repitch unit 62 to the continuous elastic band 54 and are applied in longitudinally spaced position on areas of the continuous elastic band 54 where glue layers have been previously applied, so that the individual absorbent bodies 12 are attached by glue to the continuous elastic band 54.

Figure 9:
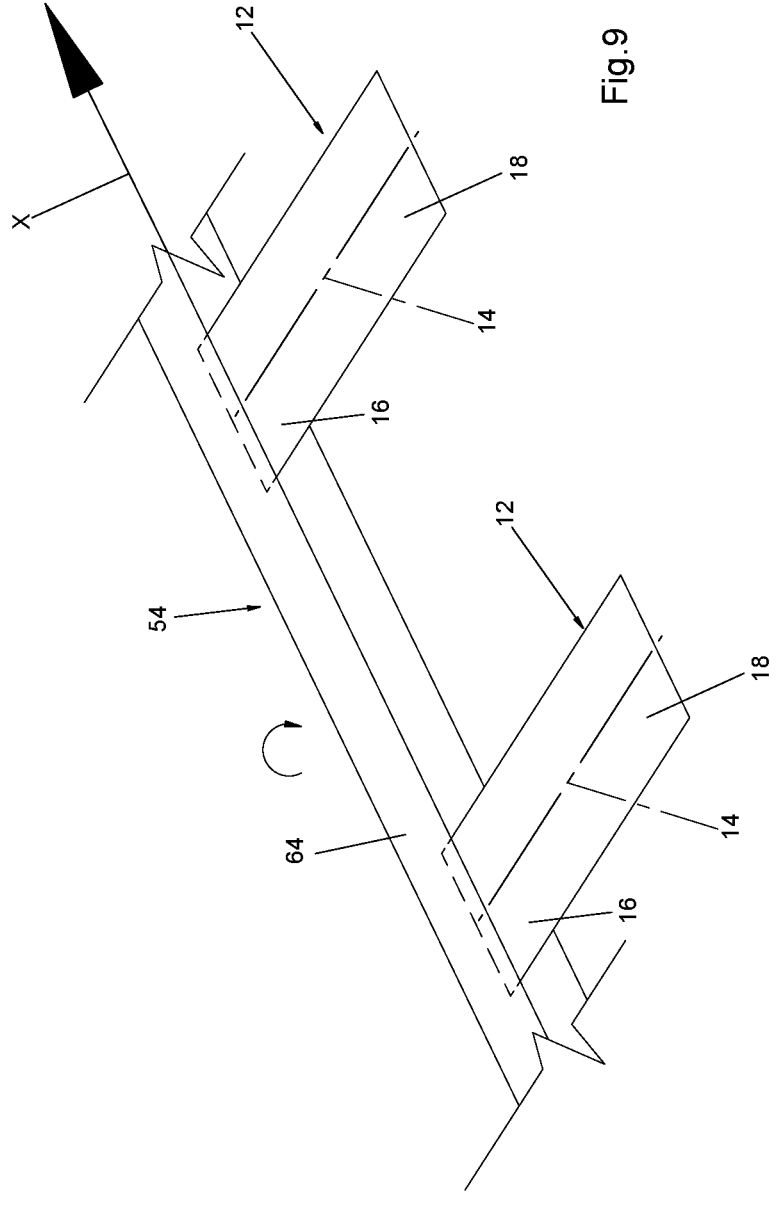
FIGS. 9-14 are schematic views showing various steps of a method for producing absorbent sanitary articles.

FIG. 9 schematically shows the continuous elastic band 54 after the attachment thereon of the absorbent bodies 12 in longitudinally spaced positions. The absorbent bodies 12 are oriented with the respective main directions 14 orthogonal to the longitudinal direction X of the continuous elastic band 54. The absorbent bodies 12 project transversally from the continuous elastic band 54. The first end portions 16 of the absorbent bodies 12 are attached to the continuous elastic band 54 and the second end portions 18 project freely from the continuous elastic band 54. The continuous elastic band 54 may have a longitudinal edge portion 64 of non-woven material which may be folded about a longitudinal folding line to overlap the transverse edges of the absorbent bodies 12. Elastic elements may be inserted in the folded longitudinal edge portion 64 to form a gasketing formation along the outer edges of the waistbands.

With reference to FIG. 8, the apparatus 50 comprises two closure element application units 66, 68, configured for applying on the continuous elastic band 54 first and second refastenable closure elements 34, 36 in spaced apart positions along the longitudinal axis X. The first and second refastenable closure elements 34, 36 may be formed by transversely cutting respective continuous webs unwound from respective reels.

Figure 10:
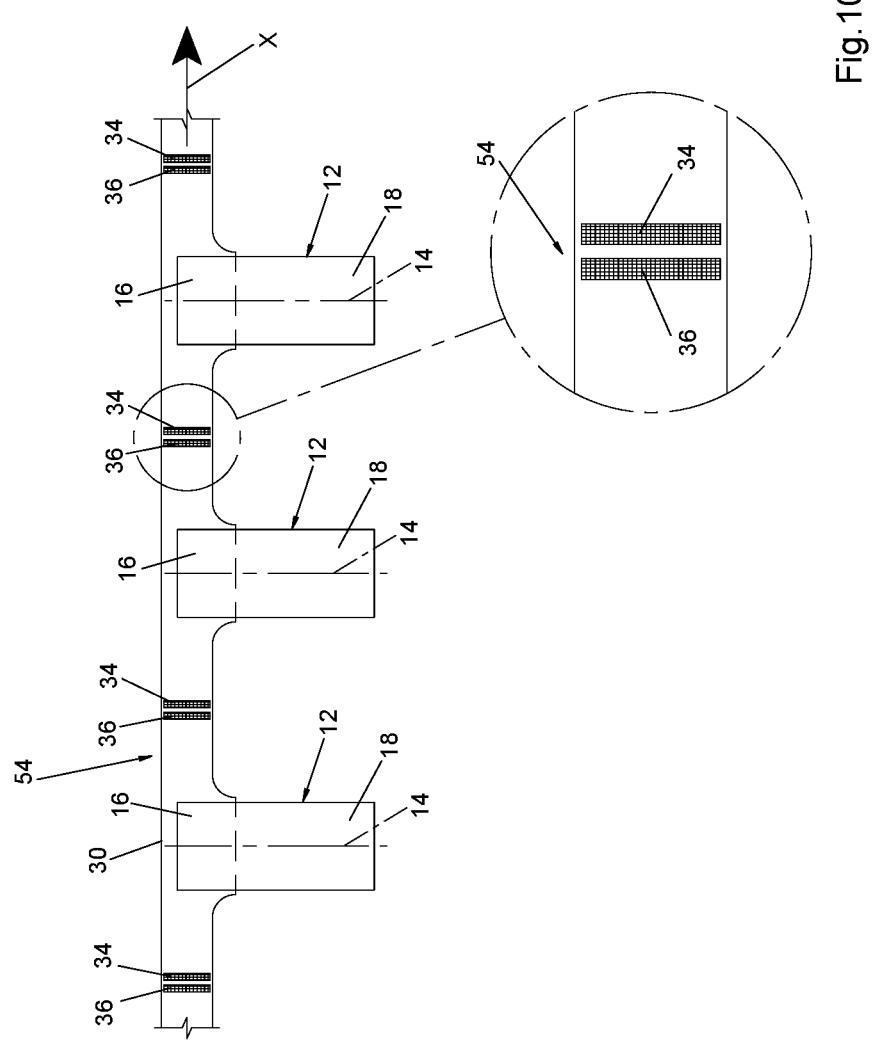

FIG. 10 shows the continuous elastic band 54 with the first and second refastenable closure elements 34, 36 applied thereon. As shown in FIG. 10, the first and second refastenable closure elements 34, 36 are arranged in pairs, each pair being formed by one first closure element 34 and one second closure element 36 parallel and close to each other and transverse to the longitudinal direction X of the continuous elastic band 54. Each pair of first and second refastenable closure elements 34, 36 is applied to the continuous elastic band 54 in a position intermediate between two adjacent absorbent bodies 12. The first and second refastenable closure elements 34, 36 may be fixed to the continuous elastic band 54 by glue and/or welding (thermocompression or ultrasonic welding).

When two closure element application units 66, 68 are provided, the first closure element application unit 66 applies the first refastenable closure elements 34 and the second closure element application unit 66 applies the second refastenable closure elements 36. In a possible embodiment, the apparatus 50 may comprise a single closure element application unit 62 or 64 configured for applying simultaneously pairs of first and second refastenable closure elements 34, 36.

With reference to FIG. 8, the apparatus 50 may comprise a longitudinal cutting unit 70 configured for cutting the longitudinal edge 32 of the continuous elastic band 54 along a shaped profile designed to conform to the legs of the user. The longitudinal cut of the longitudinal edge of the continuous elastic band 54 may be carried out before or after applying the pairs of first and second closure elements 34, 36. FIG. 10 shows the continuous elastic band 54 after the application of the pairs of first and second closure elements 34, 36 and after the longitudinal cut of the longitudinal edge 32.

Figure 11:
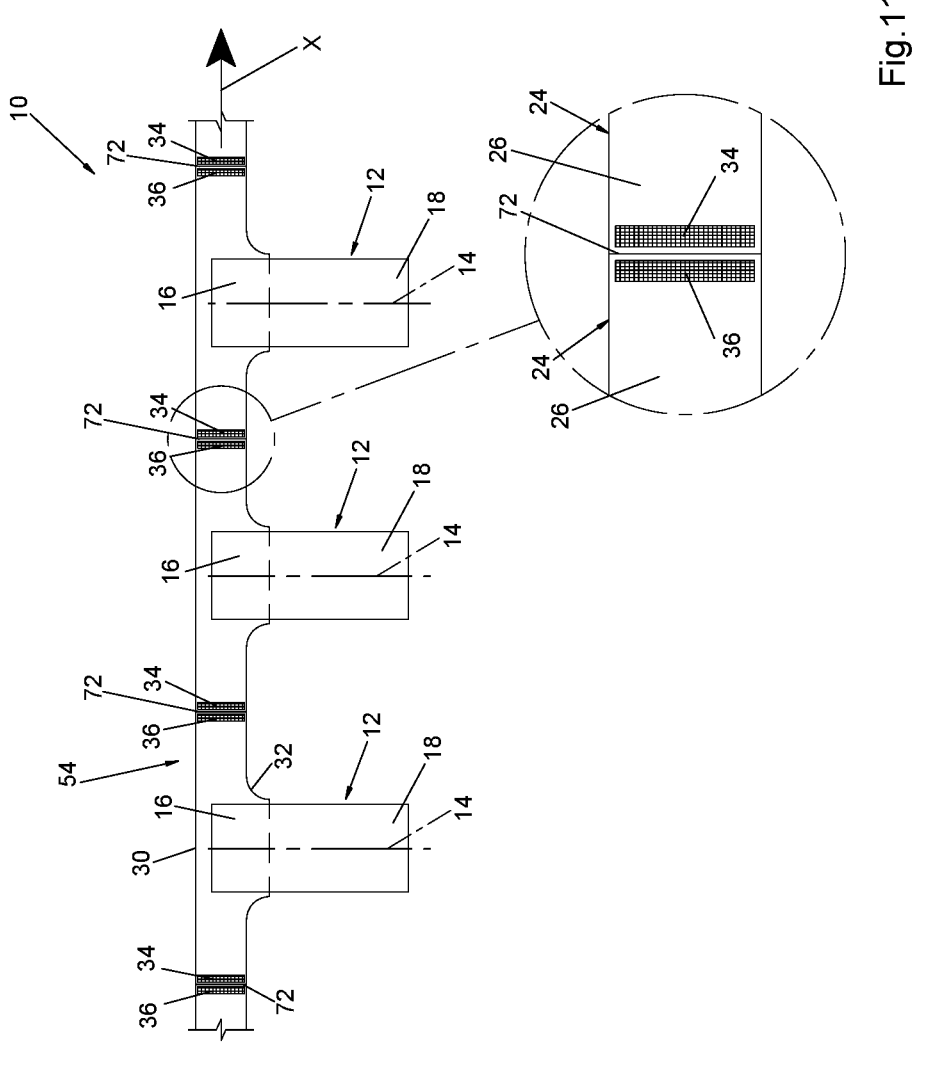

With reference to FIG. 11, the continuous elastic band 54 is cut along transverse cutting lines 72 extending between each pair of first and second closure elements 34, 36 to form a succession of individual refastenable absorbent sanitary article 10 in an outspread configuration.

With reference to FIG. 8, the apparatus 50 comprises a folding unit 74 configured for folding in a pant-like configuration the individual refastenable absorbent sanitary articles 10 initially in an outspread configuration.

With reference to FIG. 8, the folding unit 74 may comprise a rotating knife 80 configured for transversally cutting the continuous elastic band 54 on the rotating drum 76 to form the succession of individual absorbent sanitary articles 10 in outspread configuration. In a possible embodiment, the continuous elastic band 54 may be cut upstream of the folding unit 74 so that the rotating drum 76 receives a flow of individual absorbent sanitary articles 10 in outspread configuration.

Figure 12:
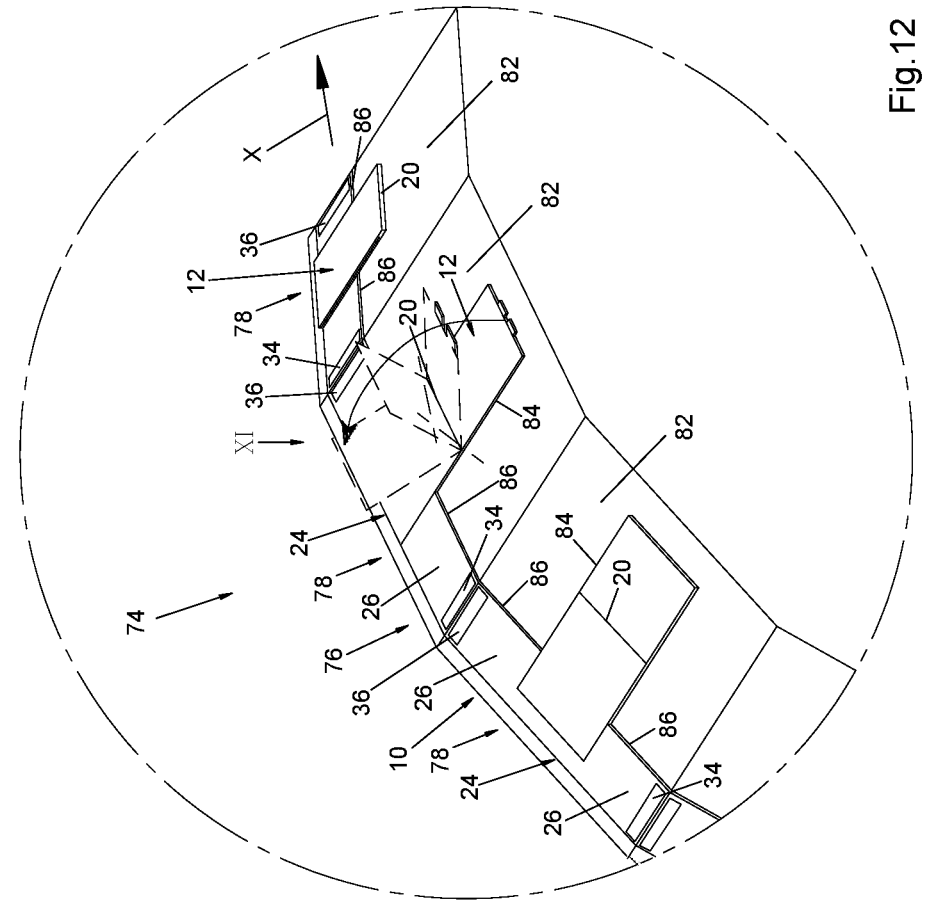
Figure 13:
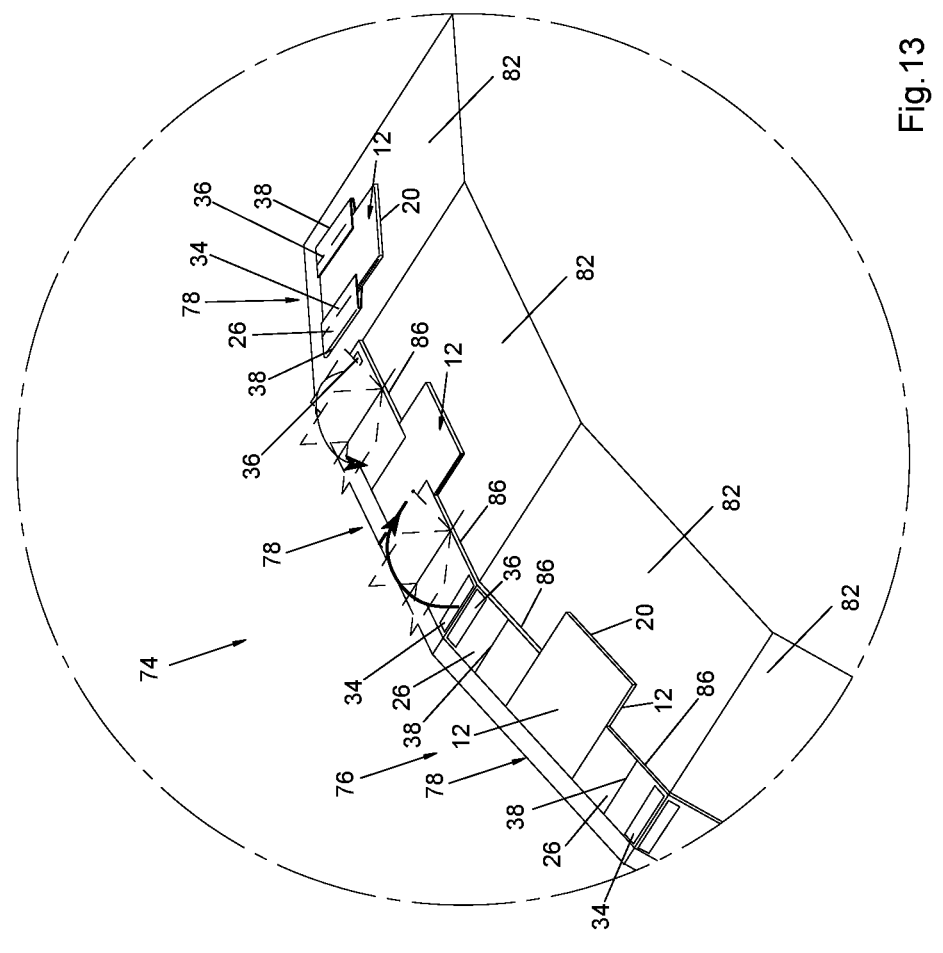

With reference to FIGS. 8 and 12, 13, the folding unit 74 comprises a rotating drum 76 carrying a plurality of folding stations 78 each of which is configured for receiving respective individual absorbent sanitary articles 10 in the outspread configuration.

With reference to FIGS. 12 and 13, each folding station 78 comprises a base 82 configured for receiving and retaining, e.g. by suction holes, a respective absorbent sanitary article 10 in the outspread configuration. Each folding station 78 comprises at least one longitudinal folding shoe 84 articulated to the base 82 and configured for folding the respective absorbent body 12 of the respective absorbent sanitary article 10 about the first folding line 20.

Each folding station 78 comprises two transverse folding shoes 86 articulated to the base 82 and configured for folding the two lateral bands 26 of the respective absorbent sanitary article 10 about respective second folding lines 38 to close the absorbent sanitary article 10 in a pant-like configuration. When the two lateral bands 26 are folded about the respective folding lines 38 the first and second refastenable closure elements 34, 36 are overlapped to the respective engagement areas 40, 42 and establish a surface connection therewith.

Figure 14:
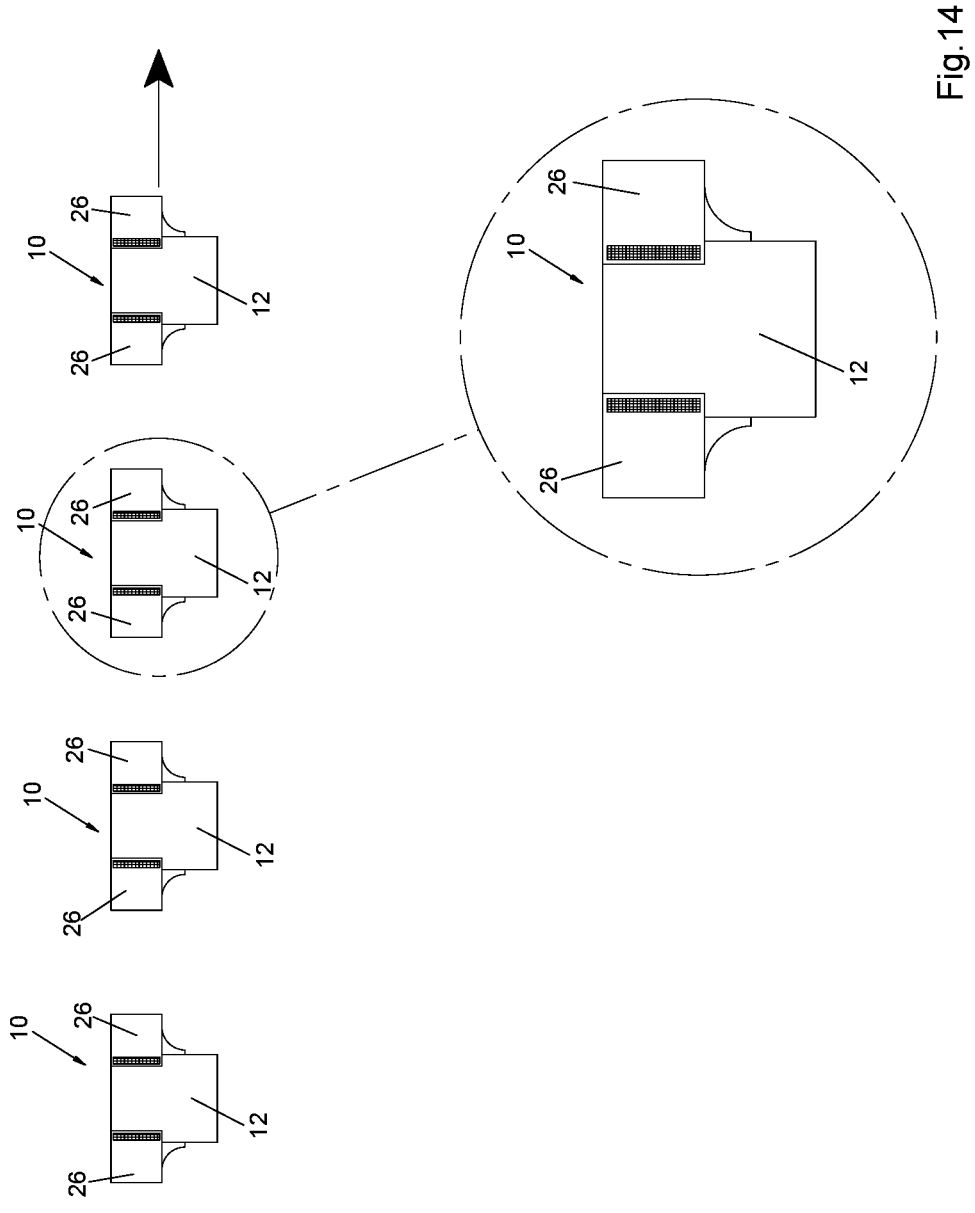

FIG. 14 shows the array of finished refastenable absorbent sanitary articles 10 closed in a pant-like configuration at the exit of the folding unit 74.

Figures 15, 16:
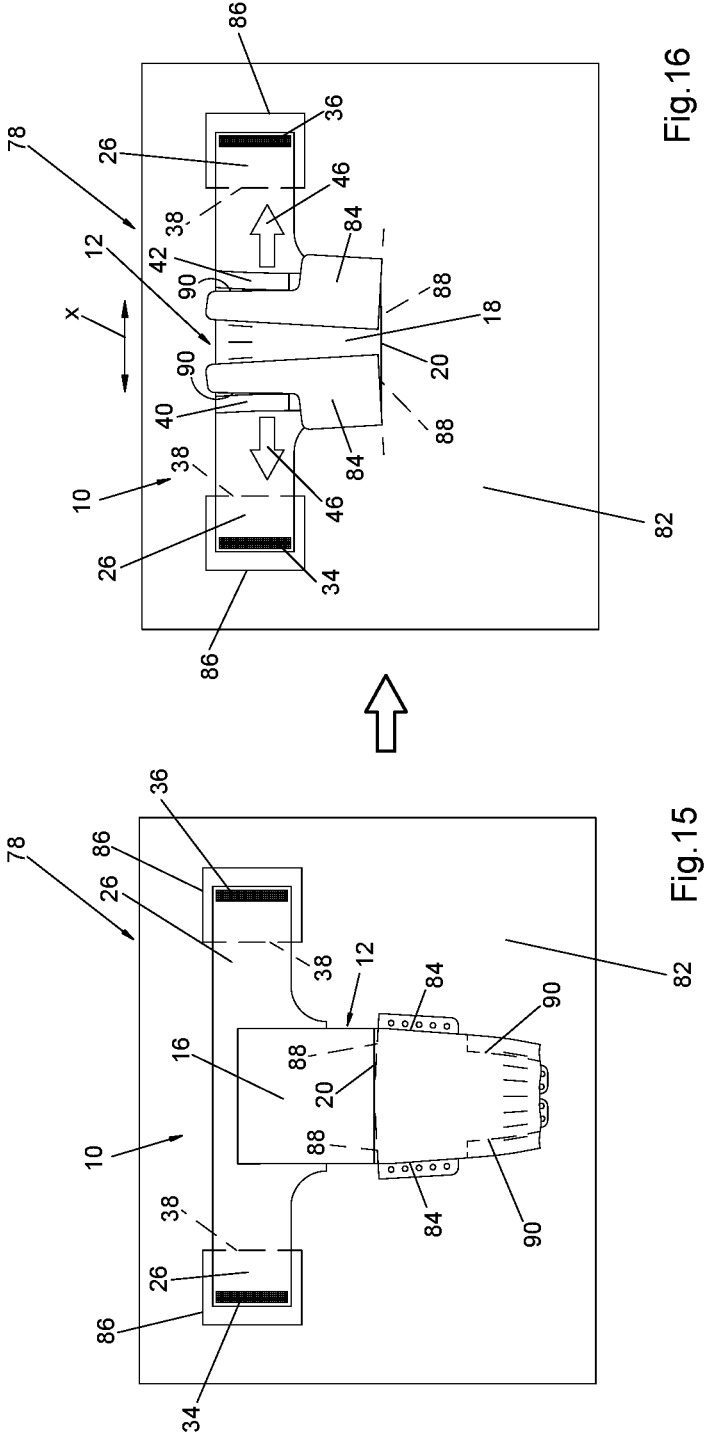
FIGS. 15 and 16 are schematic plan views showing a first embodiment of a folding station used in the method for producing absorbent sanitary articles.

FIGS. 15 and 16 show a first embodiment of a folding station 78 configured for folding the respective absorbent body 12 about the first folding line 20 and for simultaneously stretching in the longitudinal direction X the distal portions of the respective second end portion 18.

The folding station 78 comprises two longitudinal folding shoes 84 articulated to the base 82 about respective axes 88 inclined with respect to each other. The two longitudinal folding shoes 84 are provided with holes connected to a source of sub-atmospheric pressure, to retain by suction respective sections of the respective second end portions 18. The base 82 is also provided with suction holes to retain by suction the refastenable absorbent sanitary article 10 in the outspread position shown in FIG. 15.

During the rotation of the two longitudinal folding shoes 84 about the respective axes 88, the two longitudinal folding shoes 84 overlap the second end portion 18 to the respective first end portion 16, as shown in FIG. 16. Since the two longitudinal folding shoes 84 rotate about respective axes inclined with respect to each other the distal end of the respective second end portion 18 is stretched in the direction indicated by the arrows 46 in FIG. 18.

In the embodiment of FIGS. 15 and 16, the two longitudinal folding shoes 84 have respective side openings 90 which leave exposed the respective engagement areas 40, 42 of the second end portion 18. In this embodiment, after folding the second end portion 18 over the respective first end portion 16 the longitudinal folding shoes 84 continue to hold the second end portion 18 while the transverse folding shoes 86 fold the respective elastic lateral bands 26 around the respective second folding lines 38 and the first and second refastenable closure elements 34, 36 engage the respective engagement areas 40, 42 through the side openings 90 of the longitudinal folding shoes 84. After the first and second refastenable closure elements 34, 36 engage the respective engagement areas 40, 42, the longitudinal folding shoes 84 and the transverse folding shoes 86 release the second end portion 18 and the elastic lateral bands 26 and return to the position of FIG. 15 in which they are coplanar to the base 82.

Figures 17, 18:
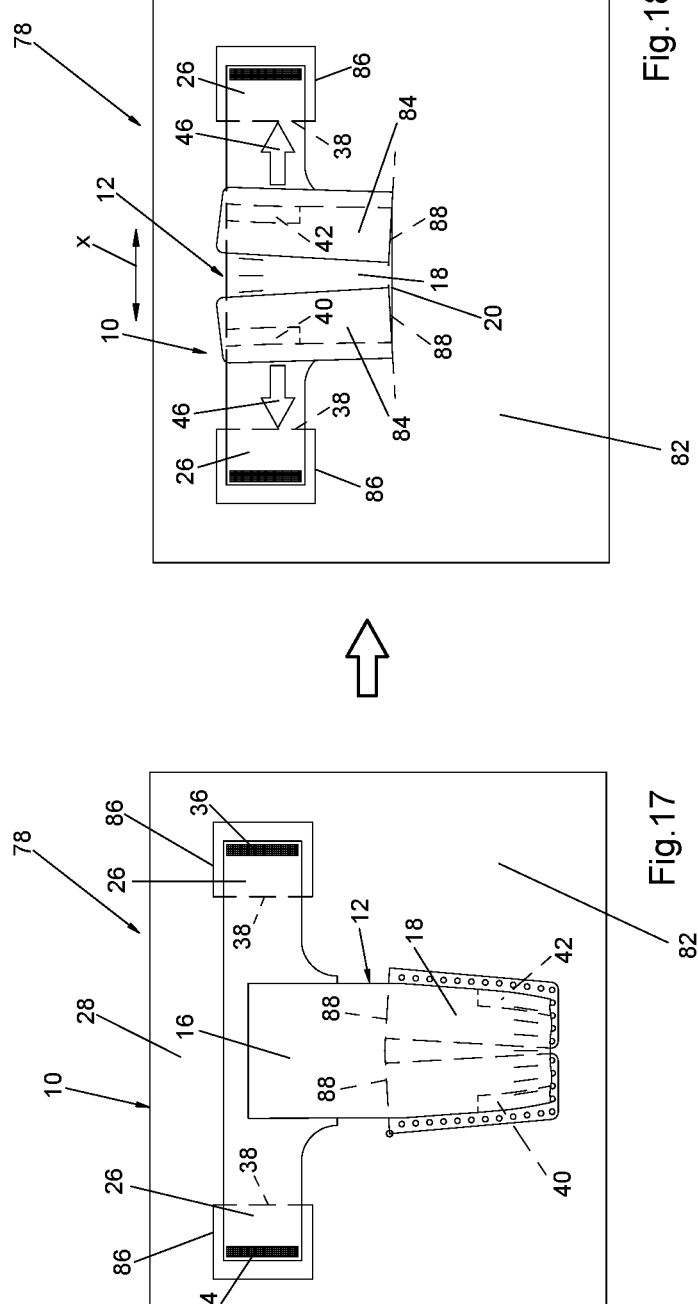
FIGS. 17 and 18 are schematic plan views showing a second embodiment of a folding station used in the method for producing absorbent sanitary articles.

FIGS. 17 and 18 show a second embodiment of a folding station 78 configured for folding the respective absorbent body 12 about the first folding line 20 and for simultaneously stretching in the longitudinal direction X the distal portions of the respective second end portion 18. The elements corresponding to those previously disclosed are indicated by the same reference numbers.

In this second embodiment, the two longitudinal folding shoes 84 differ from the longitudinal folding shoes 84 of the first embodiment in that no side openings are provided. In this embodiment, after folding the second end portion 18 over the respective first end portion 16 the longitudinal folding shoes 84 cover the engagement areas 40, 42 of the second end portion 18, as shown in FIG. 18.

In this embodiment, after folding the second end portion 18 over the respective first end portion 16 and simultaneously stretching in the direction X the distal edge of the second end portion 18 as shown in FIG. 18, the longitudinal folding shoes 84 release the second end portion 18 and return to the position of FIG. 17. The second end portion 18 is held in the folded position in that the distal edge of the second end portion 18 is in direct contact with the central portion 28 of the elastic waistband 24. Since the elastic waistband 24 is porous, the distal edge of the second end portion 18 is retained by suction by the base 82.

In this embodiment, after the longitudinal folding shoes 84 disengage from the second end portion 18 the transverse folding shoes 86 fold the respective elastic lateral bands 26 around the respective second folding lines 38 and overlap the first and second refastenable closure elements 34, 36 to the respective engagement areas 40, 42 to close the refastenable absorbent sanitary article 10 in the pant-like configuration.

The rotations of the longitudinal and transverse folding shoes 84, 86 about the respective axes 88, 38 may be controlled by cams or by actuators, which control the movement of the longitudinal and transverse folding shoes 84, 86 depending on the angular position of the rotating drum 76.

In a possible embodiment, a micro-hook front panel including a plurality of micro-hooks may be provided on a portion of the outer surface of the backsheet in the first end portion 16 of the absorbent body 12 and the distal portions of the elastic lateral bands 26 may be provided with micro-loop material (e.g. a non-woven layer or micro-loop pads) suitable for establishing a refastenable connection with the micro-hooks of the front panel. The micro-hook front panel may be integrally formed on a portion of the outer surface of the backsheet, as disclosed in EP21181365.4 of the same applicant (not yet published at the filing date of this application).

Of course, without prejudice to the principle of the invention, the details of construction and the embodiments may be widely varied with respect to those described and illustrated here, without departing from the scope of the invention as defined by the claims that follow.

The invention claimed is:
1. A method for producing refastenable pant-like absorbent sanitary articles, comprising:
    providing a single continuous elastic band having a longitudinal direction,
    providing a plurality of absorbent bodies having respective main directions and first and second end portions, orienting said plurality of absorbent bodies with the respective main directions transverse to the longitudinal direction of said single continuous elastic band, attaching the first end portions of said plurality of absorbent bodies to said single continuous elastic band in positions spaced apart from each other along said longitudinal direction, with the main directions of the plurality of absorbent bodies extending transversally to said longitudinal axis, cutting said single continuous elastic band to form a plurality of refastenable absorbent sanitary articles in an outspread configuration, each including:

an absorbent body of the plurality of absorbent bodies having the main direction and the first and second end portions, a single elastic waistband attached to the first end portion of the absorbent body and having two elastic lateral bands projecting laterally from the absorbent body, folding each absorbent body of said refastenable absorbent sanitary articles in the outspread configuration and overlapping the second end portion to the first end portion, the folding including folding each absorbent body about a first folding line and simultaneously stretching in the longitudinal direction a distal portion of the second end portion of each absorbent body, and folding the two elastic lateral bands of each absorbent sanitary article of the plurality of absorbent sanitary articles in the outspread configuration and attaching distal ends of said two elastic lateral bands to respective engagement areas of the second end portion of the absorbent body to form a refastenable absorbent sanitary article closed in a pant-like configuration.

2. The method of claim 1, comprising:

providing a continuous composite absorbent web fed in a moving direction and including a continuous absorbent core enclosed between a continuous backsheet and a continuous topsheet, transversely cutting the continuous composite absorbent web to form the plurality of absorbent bodies having respective main directions parallel to the moving direction, turning individual absorbent bodies of the plurality of absorbent bodies by 90° to orient the individual absorbent bodies with the respective main directions transverse to the moving direction, spacing from each other the individual absorbent bodies at an application pitch, and applying the individual absorbent bodies to said single continuous elastic band in longitudinally spaced positions.

3. The method of claim 2, wherein the first end portions of the individual absorbent bodies are attached to the single continuous elastic band and the second end portions project freely from the single continuous elastic band.

4. The method of claim 1, wherein the single continuous elastic band has a longitudinal edge portion of non-woven material, and wherein the method comprises folding said longitudinal edge portion about a longitudinal folding line to overlap transverse edges of the individual absorbent bodies attached to the single continuous elastic band.

5. The method of claim 4, comprising inserting elastic elements in the folded longitudinal edge portion to form gasketing formations along outer edges of the single elastic waistbands of said absorbent sanitary article in the outspread configuration.

6. The method of claim 1, comprising holding said refastenable absorbent sanitary articles in the outspread configurations on respective folding stations provided on a rotating drum, and folding said absorbent bodies and said two elastic lateral bands while the respective refastenable absorbent sanitary articles in the outspread configurations are held on the respective folding stations.

7. The method of claim 1, comprising folding the absorbent bodies of each of said refastenable absorbent sanitary articles in the outspread configurations about said first folding line by two longitudinal folding shoes articulated to a base of said folding station about respective axes inclined with respect to each other.

8. The method of claim 1, comprising attaching pairs of first and second refastenable closure elements to said single continuous elastic band in positions intermediate between absorbent bodies of said plurality of absorbent bodies, and cutting said single continuous elastic band between each pair of first and second refastenable closure elements.

* * * * *